(12) United States Patent
Nakatani et al.

(10) Patent No.: US 10,890,572 B2
(45) Date of Patent: Jan. 12, 2021

(54) MOUTHFEEL EVALUATION METHOD AND MOUTHFEEL EVALUATION APPARATUS FOR ORALLY DISINTEGRATING TEST OBJECT

(71) Applicant: SAWAI PHARMACEUTICAL Co., Ltd., Osaka (JP)

(72) Inventors: Masatoshi Nakatani, Osaka (JP); Masaru Sugita, Osaka (JP); Nobuaki Ikeji, Osaka (JP); Hiroaki Kikuoka, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 171 days.

(21) Appl. No.: 16/258,317

(22) Filed: Jan. 25, 2019

(65) Prior Publication Data
US 2019/0154647 A1    May 23, 2019

Related U.S. Application Data

(63) Continuation of application No. PCT/JP2017/026761, filed on Jul. 25, 2017.

(30) Foreign Application Priority Data

Jul. 28, 2016 (JP) ................................ 2016-148035

(51) Int. Cl.
*G01N 33/02* (2006.01)
*G01N 3/00* (2006.01)
(Continued)

(52) U.S. Cl.
CPC .............. *G01N 33/02* (2013.01); *G01N 3/00* (2013.01); *G01N 3/08* (2013.01); *G01N 3/40* (2013.01);
(Continued)

(58) Field of Classification Search
None
See application file for complete search history.

(56) References Cited

U.S. PATENT DOCUMENTS 4,108,823 A * 8/1978 Yoshimura .............. C08L 23/20
                                                         523/120
7,141,365 B2 * 11/2006 Szymkowski .......... A61P 11/00
                                                         435/6.14
(Continued)

FOREIGN PATENT DOCUMENTS

EP          1944605 A1    7/2008
JP       2003-189802 A    7/2003
(Continued)

OTHER PUBLICATIONS

Yoshiyuki Nouchi et al., "Bite-speed Effects in Two-bite Texture Analysis", Nippon Shokuhin Kagaku Kogaku Kaishi vol. 59, No. 2, 96-103 (2012), with English abstract.
(Continued)

*Primary Examiner* — Natalie Huls
*Assistant Examiner* — Jermaine L Jenkins
(74) *Attorney, Agent, or Firm* — Hauptman Ham, LLP

(57) ABSTRACT

A mouthfeel evaluation method for an orally disintegrating test object is provided, the method including, by a measurement apparatus, giving a predetermined distortion with a predetermine cycle as applying a predetermined pressure to the orally disintegrating test object, adding a predetermined amount of a test liquid to the test object, and measuring a loss tangent of the test object with time.

14 Claims, 12 Drawing Sheets

(51) Int. Cl.
*G01N 3/08* (2006.01)
*G01N 3/40* (2006.01)
*G01N 13/00* (2006.01)

(52) U.S. Cl.
CPC ....... *G01N 13/00* (2013.01); *G01N 2013/006* (2013.01)

(56) References Cited

U.S. PATENT DOCUMENTS

| | | | |
|---|---|---|---|
| 9,789,066 B2 * | 10/2017 | Szymczak | A61K 31/167 |
| 10,049,602 B2 * | 8/2018 | Michiwaki | G09B 23/32 |
| 10,493,026 B2 * | 12/2019 | Koll | A61K 9/2081 |
| 2020/0196625 A1 * | 6/2020 | Yamabe | A23G 3/34 |

FOREIGN PATENT DOCUMENTS

| | | |
|---|---|---|
| JP | 2006-129783 A | 5/2006 |
| JP | 2007-155589 A | 6/2007 |
| JP | 2011-132190 A | 7/2011 |
| JP | 2014-45713 A | 3/2014 |
| WO | 2013/027445 A1 | 2/2013 |

OTHER PUBLICATIONS

International Search Report (PCT/ISA/210) dated Oct. 24, 2017 for the PCT application No. PCT/JP2017/026761, With English translation.

Written Opinion of the International Search Authority dated Oct. 24, 2017 for the PCT application No. PCT/JP2017/026761.

English translation of Written Opinion of the International Search Authority dated Oct. 24, 2017 for the PCT application No. PCT/JP2017/026761.

Office Action issued for corresponding Japanese Patent Application No. 2018-529888 dated Nov. 24, 2020, along with an English machine translation.

* cited by examiner

MOUTHFEEL EVALUATION METHOD AND MOUTHFEEL EVALUATION APPARATUS FOR ORALLY DISINTEGRATING TEST OBJECT

CROSS REFERENCE TO RELATED APPLICATIONS

This application is based upon and claims the benefit of priority from the prior Japanese Patent Application No. 2016-148035, filed on Jul. 28, 2016, and PCT Application No. PCT/JP2017/026761, filed on Jul. 25, 2017, the entire contents of which are incorporated herein by reference.

FIELD

The present invention relates to mouthfeel evaluation methods and mouthfeel evaluation apparatuses in a simulated intraoral environment. In particular, the present invention relates to an evaluation method and evaluation apparatus for evaluating a mouthfeel of orally disintegrating food in an oral cavity such as drugs including an orally disintegrating tablet, powder, granule, and tablet sweets and so forth.

BACKGROUND

Orally disintegrating tablets are solid products which orally disintegrate quickly with saliva in the oral cavity or a small amount of water and are easily taken. Thus, demands for orally disintegrating tablets that are easily taken by patients have been increasing. On the other hand, unlike normal tablets to be swallowed with water, the mouthfeel and the feeling of residue (feeling on the tongue) at the time of oral disintegration have great influences on how easy patients can take the orally disintegrating tablets. How easy the orally disintegrating tablet can be taken is evaluated generally by an organoleptic test. However, due to variations depending on the difference among human individuals to be tested and physical conditions, it is difficult to achieve reproducibility and is difficult to say this is an appropriate evaluation method.

Moreover, in an orally disintegrating tablet containing a highly-active drug substance, it is difficult to evaluate the tablet in the human oral cavity. As a method of safely and objectively evaluating a taste such as bitterness of the orally disintegrating tablet, a taste sensor is being introduced. However, methods of safely and objectively evaluating a mouthfeel and a feeling of residue (feeling on the tongue) at the time of oral disintegration have not been reported so far. Therefore, an evaluation method for replacing a method of evaluating a mouthfeel and a feeling of residue (feeling on the tongue) in the human oral cavity has been desired.

As one objective food-mouthfeel evaluation method, a method using autograph (universal tester, mouthfeel analyzer) has been known. For example, in standards regarding "hardness", "adhesion property", and "cohesiveness" of "foods for people with difficulty in swallowing" under the charge of Consumer Affairs Agency, 2-byte mouthfeel test has been performed. However, foods for people with difficulty in swallowing are mainly semi-solid foods which are uniform such as jelly, and this test cannot evaluate the mouthfeel and the feeling of residue when the orally disintegrating tablet disintegrates with saliva in the oral cavity or a small amount of water. The reason for this is that in the orally disintegrating tablet, a powder drug substance and an additive made into a tablet disintegrate by absorbing saliva in the oral cavity or a small amount of water to acquire fluidity for allowing swallowing and thus changes in their states have an influence on the mouthfeel and the feeling of residue. Nippon Shokuhin Kagaku Kogaku Kaishi Vol. 59, No. 2, 96-103 (2012)

SUMMARY

Methods of safely and objectively evaluating a disintegration process by absorbing saliva in the oral cavity or a small amount of water, a mouthfeel, and a feeling of residue have not been reported so far. If this method is achieved, a disintegration process, a mouthfeel, and a feeling of residue can be evaluated not only for orally disintegrating tablets but also for drugs such as powder and granule and tablet sweets such as refreshing sweets and mint tablets.

One object of the present invention is to provide an evaluation method for evaluating a mouthfeel of orally disintegrating drugs and foods such as orally disintegrating tablets and tablet sweets in a simulated intraoral environment. Another object of the present invention is to provide an evaluation apparatus for evaluating a mouthfeel of drugs such as orally disintegrating tablets, powder, and granule and, furthermore, orally disintegrating foods such as tablet sweets in a simulated intraoral environment.

According to one embodiment of the present invention, a mouthfeel evaluation method for an orally disintegrating test object is provided, the method including, by a measurement apparatus, giving a predetermined distortion with a predetermine cycle as applying a predetermined pressure to the orally disintegrating test object, adding a predetermined amount of a test liquid to the test object, and measuring a loss tangent of the test object with time.

In the mouthfeel evaluation method for the test object, when a jig of ϕ12 mm is used, the pressure to be applied to the test object may be larger than 1 N and smaller than 10 N.

In the mouthfeel evaluation method for the test object, the distortion equal to or larger than 0.1% and equal to or smaller than 20% may be given to the test object with a cycle equal to or larger than 0.5 Hz and equal to or smaller than 5 Hz.

In the mouthfeel evaluation method for the test object, the test liquid equal to or larger than 50% of an amount absorbable by the test object may be added.

In the mouthfeel evaluation method for the test object, a mouthfeel may be evaluated with a value of the loss tangent until the test object disintegrates, and a feeling of residue may be evaluated with a value after the test object disintegrates.

Also, according to one embodiment of the present invention, a mouthfeel evaluation apparatus for an orally disintegrating test object is provided, the apparatus including a viscoelasticity measurement unit which gives a predetermined distortion with a predetermine cycle as applying a predetermined pressure to the orally disintegrating test object and measures a loss tangent of the test object with time, a test liquid supply unit which adds a predetermined amount of a test liquid to the test object, and an analyzing unit which analyzes characteristics of the test object.

In the mouthfeel evaluation apparatus for the test object, the viscoelasticity measurement unit may include a jig of ϕ12 mm, and may apply to the test object a pressure larger than 1 N and smaller than 10 N.

In the mouthfeel evaluation apparatus for the test object, the viscoelasticity measurement unit may give to the test object a distortion equal to or larger than 0.1% and equal to or smaller than 20% with a cycle equal to or larger than 0.5 Hz and equal to or smaller than 5 Hz.

In the mouthfeel evaluation apparatus for the test object, the test liquid supply unit may add to the test object the test liquid equal to or larger than 50% of an amount absorbable by the test object.

In the mouthfeel evaluation apparatus for the test object, the analyzing unit may present a mouthfeel as a value of the loss tangent until the test object disintegrates, and may present a feeling of residue as a value after the test object disintegrates.

BRIEF DESCRIPTION OF DRAWINGS

FIG. 7A shows a diagram with distance (d) from the sample table 111 to the jig 113, the loss tangent (tan δ), and the storage elastic modulus (G') measured with any of distortions, 0.1%, 0.2%, 0.5%, 5%, 10%, 20%, or 50%, given thereto and plotted on the time axis according to one embodiment of the present invention, in which FIG. 7A shows measurement results using a sample A.

FIG. 10A shows diagrams of results of a study of the amount of a test liquid to be added at the time of measuring the distance (d) of the jig 113 from the sample table 111, the loss tangent (tan δ), and the storage elastic modulus (G') according to one embodiment of the present invention, in which FIG. 10A shows measurement results of the distance (d).

FIG. 11A shows diagrams of results of a study of the amount of a test liquid to be added at the time of measuring the distance (d) of the jig 113 from the sample table 111, the loss tangent (tan δ), and the storage elastic modulus (G') according to one embodiment of the present invention, in which FIG. 11A shows measurement results of the distance (d).

REFERENCE SIGNS LIST

1: sample; 100: evaluation apparatus; 110: viscoelasticity measurement unit; 111: sample table; 113: jig; 120: test liquid supply unit; 130: analyzing unit; 140: control unit

DESCRIPTION OF EMBODIMENTS

In the following, the mouthfeel evaluation method and mouthfeel evaluation apparatus for an orally disintegrating test object according to the present invention are described. However, the mouthfeel evaluation method and mouthfeel evaluation apparatus for an orally disintegrating test object should not be interpreted as being limited to the following description of embodiments and examples.

(Mouthfeel Evaluation Apparatus for Orally Disintegrating Test Object)

Figure 1A:
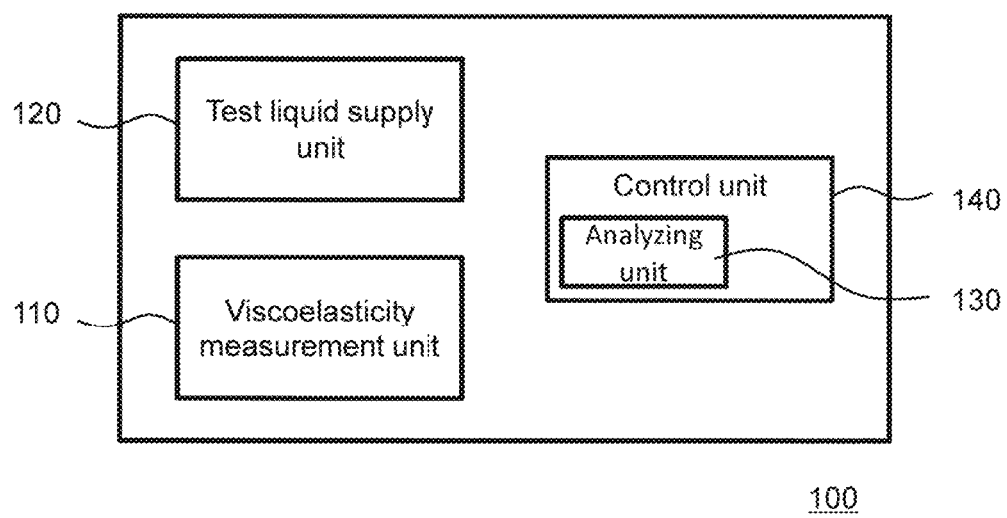
FIG. 1A shows a mouthfeel evaluation apparatus 100 for an orally disintegrating test object according to one embodiment of the present invention and is a block configuration diagram of the mouthfeel evaluation apparatus 100.
Figure 1B:
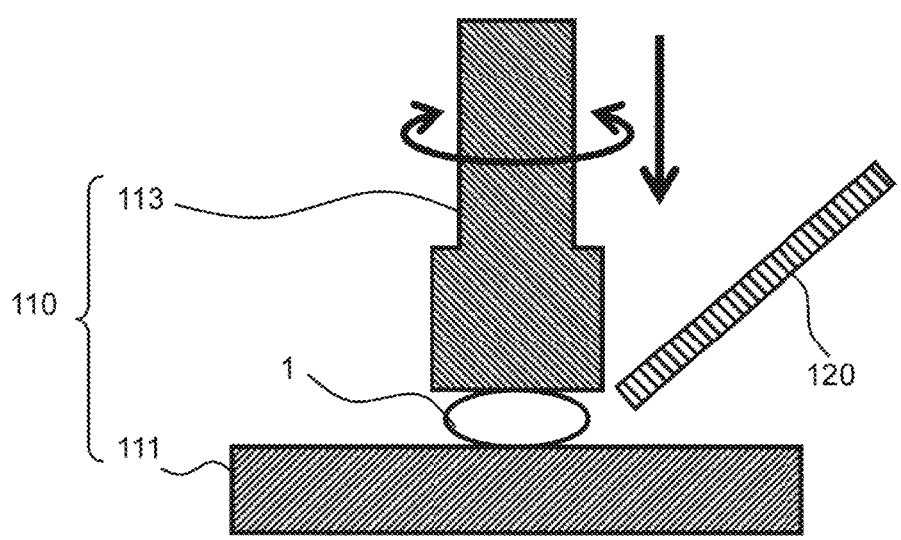
FIG. 1B is a schematic view of a viscoelasticity measurement unit 110 and a test liquid supply unit 120.

FIG. 1A and FIG. 1B show a mouthfeel evaluation apparatus 100 for an orally disintegrating test object according to one embodiment of the present invention. FIG. 1A is a block configuration diagram of the mouthfeel evaluation apparatus 100. FIG. 1B is a schematic view of a viscoelasticity measurement unit 110 and a test liquid supply unit 120. The mouthfeel evaluation apparatus 100 is a measurement apparatus which includes, for example, the viscoelasticity measurement unit 110, the test liquid supply unit 120, and an analyzing unit 130, although not limited thereto.

The viscoelasticity measurement unit 110 includes, for example, a sample table 111 and a jig 113 arranged so as to be opposed to the sample table 111. The sample table 111 is a table where an orally disintegrating test object (hereinafter also referred to as a sample 1) is arranged. The jig 113 gives a predetermined distortion with a predetermined cycle while applying a predetermined pressure to the sample 1. The viscoelasticity measurement unit 110 drives the jig 113 to sequentially measure a loss tangent (tan δ) of the sample 1.

In more detail, the viscoelasticity measurement unit 110 drives the jig 113 to measure a storage elastic modulus (G') and a loss elastic modulus (G"). The analyzing unit 130 calculates a loss tangent (tan δ) by the following equation (1) from the storage elastic modulus (G') and the loss elastic modulus (G") measured at the viscoelasticity measurement unit 110.

Loss tangent (tan δ)=loss elastic modulus (G")/storage elastic modulus (G')         (1)

Note that not the analyzing unit 130 but the viscoelasticity measurement unit 110 may calculate the loss tangent (tan δ). For example, when the viscoelasticity measurement unit 110 includes a calculation unit, the viscoelasticity measurement unit 110 can calculate the loss tangent (tan δ).

If including the jig 113 having φ12 mm, the viscoelasticity measurement unit 110 applies a pressure larger than 1 N and smaller than 10 N to the sample 1. Also, the viscoelasticity measurement unit 110 drives the jig 113 with a cycle equal to or larger than 0.5 Hz and equal to or smaller than 5 Hz to give a distortion equal to or larger than 0.1% and equal to or smaller than 20%. In one embodiment, the viscoelasticity measurement unit 110 preferably drives the jig 113 with 3 Hz and applies a pressure of 5 N to the sample 1 while giving a distortion of 5%. For example, Utanohara Y. et al., Dysphagia, 23:286-290, 2008 reports that the human tongue depression is on the order of 40 kPa, which substantially corresponds to a pressure of 5 N to be applied by the jig 113 having φ12 mm to the sample 1 being approximately 35 kPa. As the viscoelasticity measurement unit 110, a rheometer capable of satisfying the above-described measurement conditions can be used.

The test liquid supply unit 120 is arranged so as to be near the sample 1 to add a predetermined amount of a test liquid to the sample 1. While water, artificial saliva, buffer solution, or the like can be used as the test liquid, the test liquid is not meant to be limited to these. The test liquid supply unit 120 adds the test liquid equal to or more than 50% of the amount absorbable by the sample 1. To evaluate a general orally disintegrating tablet, the test liquid to be dropped from the test liquid supply unit 120 to the sample 1 is preferably 0.5 ml.

While a syringe pump, for example, can be used as the test liquid supply unit 120, this is not meant to be restrictive in the mouthfeel evaluation apparatus 100 according to the present invention. The test liquid may be dropped to the sample 1 manually dropped from a syringe, dropper, pipette, or the like. Any dropping speed of the test liquid can be set.

The analyzing unit 130 is an apparatus which analyzes data received from the viscoelasticity measurement unit 110 and is, for example, an arithmetic device which processes an analysis program. The analyzing unit 130 may be a dedicated apparatus including a ROM (Read Only Memory) having the analysis program stored therein or a general-purpose apparatus where the analysis program is stored or provided online. The analyzing unit 130 may be, for example, a personal computer (PC) or a portable terminal such as a tablet capable of executing the analysis program.

Figure 2:
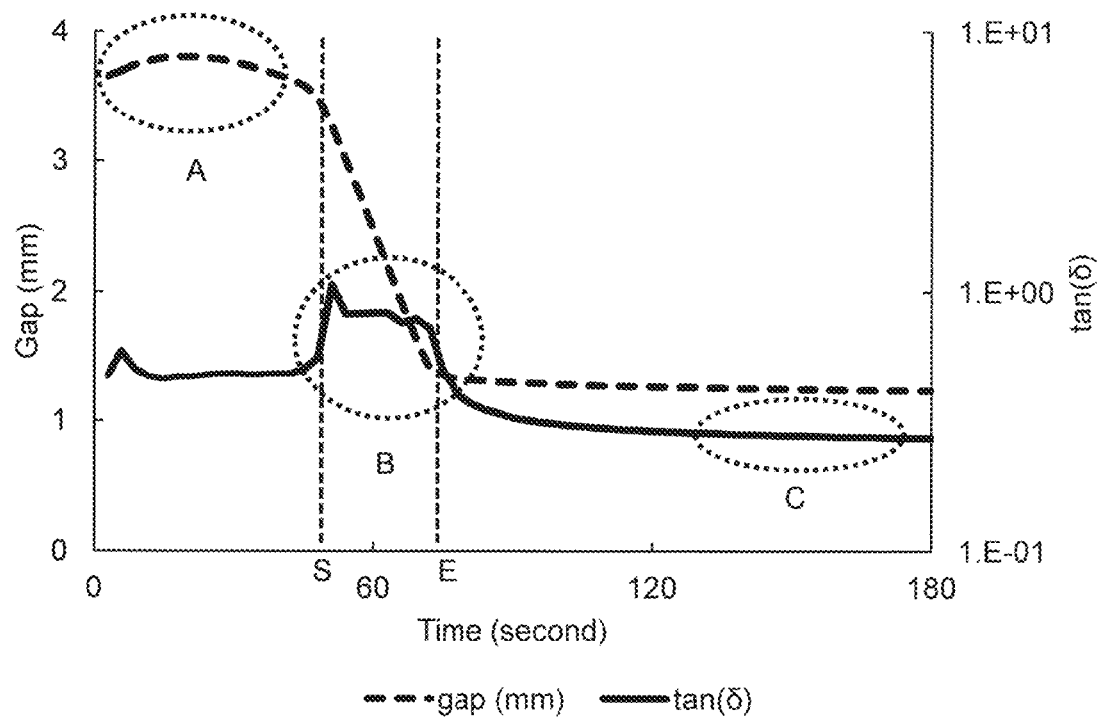
FIG. 2 is a diagram showing mouthfeels of an orally disintegrating sample 1 according to one embodiment of the present invention.

From the loss tangent (tan δ) received from the viscoelasticity measurement unit 110, the analyzing unit 130 analyzes a change in the state of the sample 1 at the time of disintegration. Based on the loss tangent (tan δ) of the sample 1 received from the viscoelasticity measurement unit 110, the analyzing unit 130 can evaluate the mouthfeel and the feeling of residue. FIG. 2 is a diagram showing mouthfeels of the orally disintegrating sample 1 according to one embodiment of the present invention. In FIG. 2, the loss tangent (tan δ) of the sample 1 is plotted with respect to the time axis. A region B of the loss tangent (tan δ) corresponds to a mouthfeel when the sample 1 orally disintegrates and a region C of the loss tangent (tan δ) corresponds to a feeling of residue after the sample 1 orally disintegrates.

In FIG. 2, together with the loss tangent (tan δ) of the sample 1, a distance (gap) to the jig 113 from the sample table 111 is plotted with respect to the time axis. A curve indicating the distance (gap) from the jig 113 indicates a tendency of going away from the sample table 111 in a region A. This is because the test liquid dropped from the test liquid supply unit 120 is absorbed by the sample 1 to swell the sample 1.

The sample 1 absorbing the test liquid starts disintegrating by pressure applied by the jig 113 (time S). Since the sample 1 abruptly disintegrates when disintegration starts, the distance (gap) to the jig 113 from the sample table 111 linearly decreases with respect to the time axis. In FIG. 2, the linear decrease of the distance (gap) to the jig 113 after the time S indicates a disintegrating speed of the sample 1. When the sample 1 disintegrates (time E), particles of powder of a drug substance, additive, and so forth contained in the sample 1 appear (remain), and these particles further disintegrate by pressure applied by the jig 113. At the time of particle disintegration, the disintegrating speed significantly decelerates, and the curve indicating the distance (gap) from the jig 113 becomes in a linear form with a mild gradient with respect to the time axis.

In this manner, the gradient of the curve indicating the distance (gap) from the jig 113 increases when the sample 1 starts disintegrating, and the gradient of the curve indicating the distance (gap) from the jig 113 decreases when the sample 1 ends disintegration (makes transition to disintegration of particles only). Times when the changes in gradient occur can be determined as the time S and the time E, respectively. Therefore, the values (the region B) of the loss tangent (tan δ) appearing in a period overlapping the period from the time S to the time E can be determined as a mouthfeel when the sample 1 orally disintegrates.

The analyzing unit 130 can evaluate an average value or a maximum value (or local maximum value) of the values (the region B) of the loss tangent (tan δ) appearing in the period overlapping the period from the time S to the time E as a mouthfeel (such as softness, smoothness, and so forth) at the time of oral disintegration of the sample 1.

Also, when the loss tangent (tan δ) with disintegration of the residual particles after the sample 1 disintegrates is smaller than that of an orally disintegrating tablet as a comparison target in the region C, this indicates a more feeling of residue (powdery mouthfeel). When the value of the loss tangent (tan δ) is larger than that of the orally disintegrating tablet as a comparison target in the region C, this indicates a feeling of melting in the mouth smoother than that of the comparison target.

The mouthfeel evaluation apparatus 100 further includes a control unit 140 which controls the viscoelasticity measurement unit 110 and the test liquid supply unit 120. The control unit 140 may be a dedicated apparatus including a ROM (Read Only Memory) having a control program for controlling the viscoelasticity measurement unit 110 and the test liquid supply unit 120 stored therein or a general-purpose apparatus where the analysis program is stored or provided online. The control unit 140 may be, for example, a personal computer (PC) or a portable terminal such as a tablet capable of executing the analysis program.

Also, the control unit 140 may include the analyzing unit 130, or may be installed in the mouthfeel evaluation apparatus 100 separately from the analyzing unit 130. Therefore, the analyzing unit 130 may be a module incorporated in the control unit 140, or may be a program executable on the control unit 140.

Furthermore, although not shown, the mouthfeel evaluation apparatus 100 includes an input apparatus such as a keyboard, a touch panel, a mouse, and so forth. A user can operate the mouthfeel evaluation apparatus 100 through the input apparatus. For example, by using the input apparatus, the user can set any amount of the test liquid to be dropped from the test liquid supply unit 120 and any dropping speed.

Still further, although not shown, the mouthfeel evaluation apparatus 100 includes a display apparatus. The mouthfeel evaluation apparatus 100 can display to the user, for example, the temporal curve of the loss tangent (tan δ) of the sample 1 and the temporal curve of the distance (gap) from the jig 113 as shown in FIG. 2, and so forth.

As described above, the mouthfeel evaluation apparatus 100 for the orally disintegrating test object according to the embodiment of the present invention can provide the temporal curve of the loss tangent (tan δ) of the sample 1, the temporal curve of the distance (gap) from the jig 113, and so forth and also can evaluate the mouthfeel and the feeling of residue at the time of oral disintegration of the sample 1.

(Mouthfeel Evaluation Method for Orally Disintegrating Test Object)

An evaluation method for an orally disintegrating test object using the above-described mouthfeel evaluation apparatus for the orally disintegrating test object is described below.

To evaluate the mouthfeel of an orally disintegrating tablet as an orally disintegrating test object, any sample 1 is prepared. In view of accuracy and reproducibility of mouthfeel evaluation, it is preferable to prepare the samples 1 as many as possible.

Figure 3:
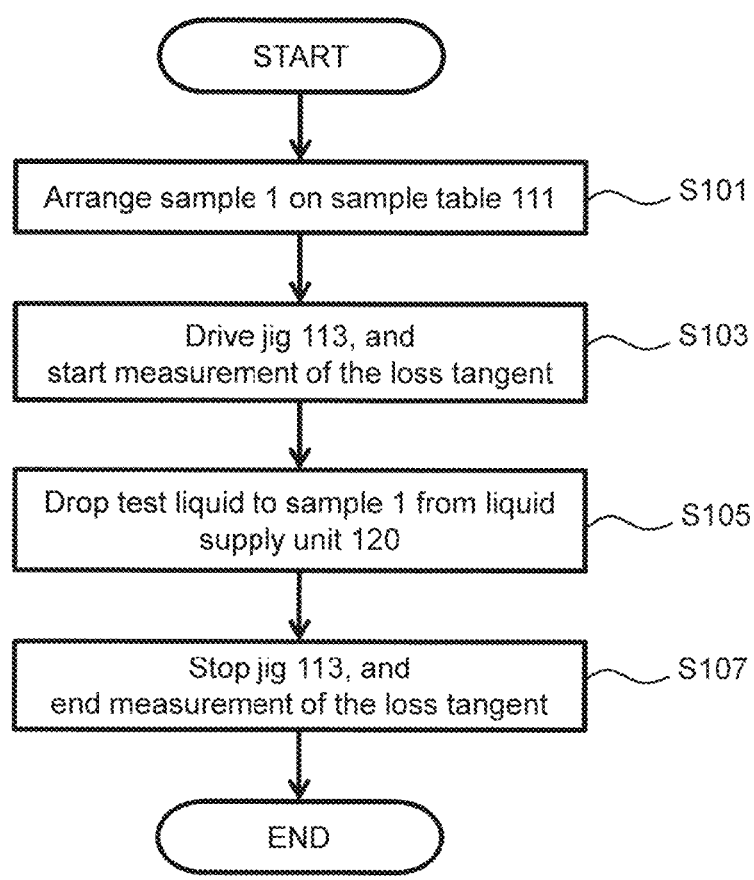
FIG. 3 is a flowchart showing a measurement method for a loss tangent (tan δ) of an orally disintegrating test object according to one embodiment of the present invention.

FIG. 3 is a flowchart showing a measurement method for a loss tangent (tan δ) of an orally disintegrating test object according to one embodiment of the present invention. The sample 1 is arranged on the sample table 111 of the viscoelasticity measurement unit 110, and is nipped by the jig 113 (S101). The jig 113 is driven to start measurement of the loss tangent (tan δ) (S103).

The viscoelasticity measurement unit 110 drives the jig 113, and applies a pressure larger than 1 N and smaller than 10 N to the sample 1. Also, the viscoelasticity measurement unit 110 drives the jig 113 in a cycle equal to or larger than 0.5 Hz and equal to or smaller than 5 Hz to give a distortion equal to or larger than 0.1% and equal to or smaller than 20%. In one embodiment, while driving the jig 113 at 3 Hz to give a distortion of 5% the viscoelasticity measurement unit 110 preferably applies a pressure of 5 N to the sample 1.

Measurement data of the loss tangent (tan δ) is transmitted from the viscoelasticity measurement unit 110 to the analyzing unit 130 for storage. Also, the viscoelasticity measurement unit 110 may drive the jig 113 to measure the storage elastic modulus (G') and the loss elastic modulus (G"). The analyzing unit 130 calculates the loss tangent (tan δ) by the following equation (1) from the storage elastic modulus (G') and the loss elastic modulus (G") at the viscoelasticity measurement unit 110.

$$\text{Loss tangent (tan δ)} = \text{loss elastic modulus } (G'')/\text{storage elastic modulus } (G') \quad (1)$$

Note that not the analyzing unit 130 but the viscoelasticity measurement unit 110 may calculate the loss tangent (tan δ). For example, when the viscoelasticity measurement unit 110 includes a calculation unit, the viscoelasticity measurement unit 110 can calculate the loss tangent (tan δ).

The test liquid equal to or more than 50% of the amount absorbable by the sample 1 is dropped from the test liquid supply unit 120 (S105). To evaluate a general orally disintegrating tablet, the test liquid to be dropped from the test liquid supply unit 120 to the sample 1 is preferably 0.5 ml.

After the sample 1 disintegrates and a predetermined time passes, the measurement of the loss tangent (tan δ) is ended (S107). To evaluate a general orally disintegrating tablet, the measurement time of the loss tangent (tan δ) is only required to be on the order of three to five minutes.

From the process described above, the loss tangent (tan δ) of the sample 1 can be evaluated. From the value of the loss tangent (tan δ) found as described above, the mouthfeel and the feeling of residue at the time of oral disintegration of the sample 1 can be evaluated.

Figure 4:
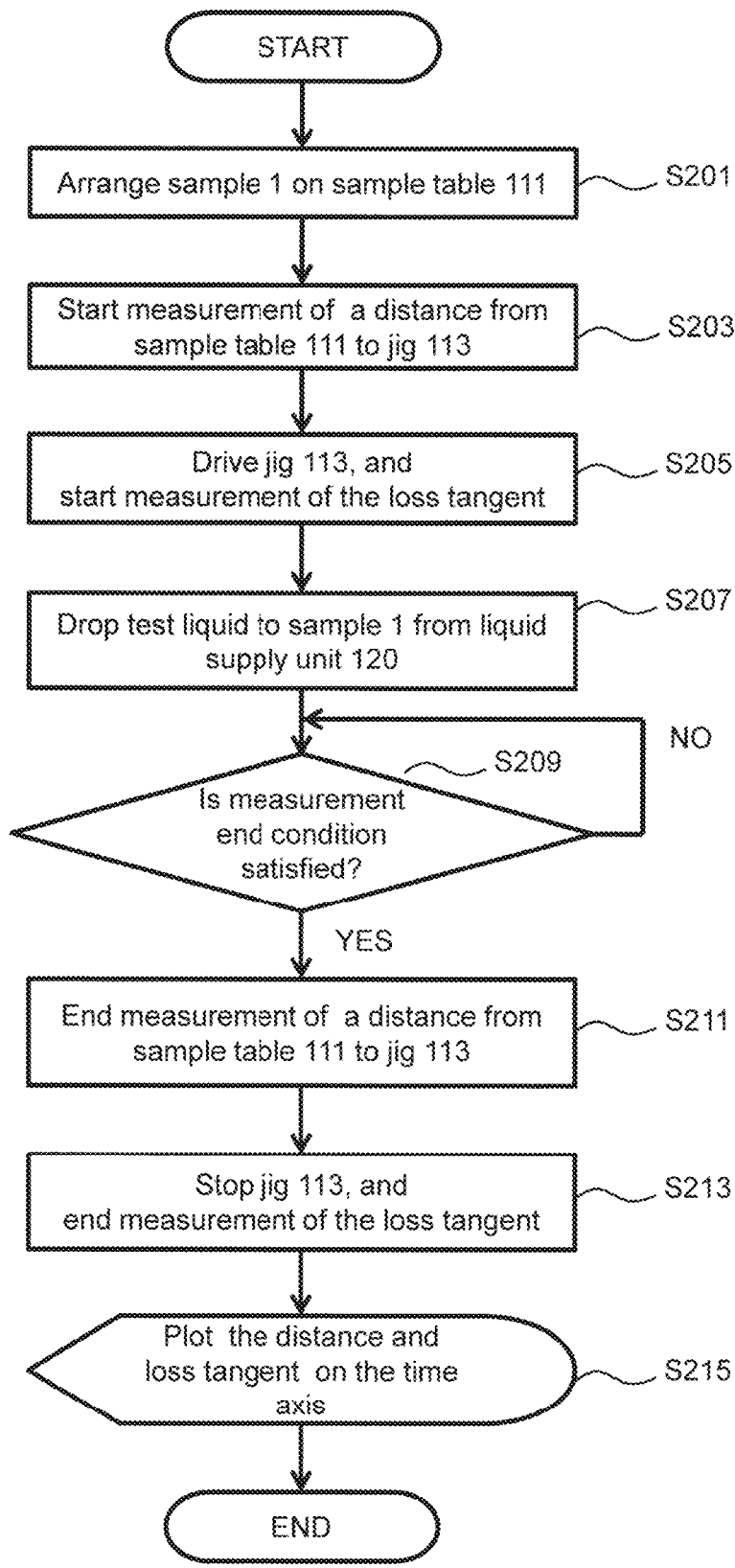
FIG. 4 is a flowchart showing a measurement method for a loss tangent (tan δ) of an orally disintegrating test object according to one embodiment of the present invention.

FIG. 4 is a flowchart showing a measurement method for a loss tangent (tan δ) of an orally disintegrating test object according to one embodiment of the present invention. The sample 1 is arranged on the sample table 111 of the viscoelasticity measurement unit 110, and is nipped by the jig 113 (S201). The viscoelasticity measurement unit 110 measures a distance from the sample table 111 to the jig 113 for transmission to the analyzing unit 130 (S203).

The jig 113 is driven to start measurement of the loss tangent (tan δ) (S205). If including the jig 113 having φ12 mm, the viscoelasticity measurement unit 110 applies a pressure larger than 1 N and smaller than 10 N to the sample 1. Also, the viscoelasticity measurement unit 110 drives the jig 113 with a cycle equal to or larger than 0.5 Hz and equal to or smaller than 5 Hz to give a distortion equal to or larger than 0.1% and equal to or smaller than 20%. In one embodiment, the viscoelasticity measurement unit 110 preferably drives the jig 113 with 3 Hz and applies a pressure of 5 N to the sample 1 while giving a distortion of 5%.

Measurement data of the loss tangent (tan δ) is transmitted from the viscoelasticity measurement unit 110 to the analyzing unit 130 for storage. Also, the viscoelasticity measurement unit 110 may drive the jig 113 to measure the storage elastic modulus (G') and the loss elastic modulus (G"). The analyzing unit 130 calculates the loss tangent (tan δ) by the following equation (1) from the storage elastic modulus (G') and the loss elastic modulus (G") at the viscoelasticity measurement unit 110.

$$\text{Loss tangent (tan δ)} = \text{loss elastic modulus } (G'')/\text{storage elastic modulus } (G') \quad (1)$$

Note that not the analyzing unit 130 but the viscoelasticity measurement unit 110 may calculate the loss tangent (tan δ). For example, when the viscoelasticity measurement unit 110 includes a calculation unit, the viscoelasticity measurement unit 110 can calculate the loss tangent (tan δ).

The test liquid equal to or more than 50% of the amount absorbable by the sample 1 is dropped from the test liquid supply unit 120 (S207). To evaluate a general orally disintegrating tablet, the test liquid to be dropped from the test liquid supply unit 120 to the sample 1 is preferably 0.5 ml.

The control unit 140 determines whether a measurement end condition is satisfied (S209). For example, when the distance from the sample table 111 to the jig 113 received by the analyzing unit 130 becomes a predetermined value, the control unit 140 determines that the measurement end condition is satisfied. Also, when the curve indicating the distance (gap) from the jig 113 plotted by the analyzing unit 130 has a predetermined gradient with respect to the time axis, that is, when particles are hardly present between the sample table 111 and the jig 113 and only powder of disintegrated particles are present and movement of the jig 113 to a direction of the sample table 111 hardly proceeds, the control unit may cause the viscoelasticity measurement unit 110 to end the measurement. The control unit 140 continues the measurement until the measurement end condition is satisfied.

When determining that the measurement end condition is satisfied, the control unit 140 causes the viscoelasticity measurement unit 110 to stop driving the jig 113, and ends the measurement of the distance from the sample table 111 to the jig 113 (S211). Also, the control unit 140 causes the viscoelasticity measurement unit 110 to end the measurement of the loss tangent (tan δ) (S213).

The analyzing unit 130 plots the distance from the sample table 111 to the jig 113 and the loss tangent (tan δ) on the time axis (S215).

By the process described above, the distance from the sample table 111 to the jig 113 and the loss tangent (tan δ) of the sample 1 can be measured. From the distance from the sample table 111 to the jig 113 and the value of the loss tangent (tan δ) found as described above, the mouthfeel and the feeling of residue at the time of oral disintegration of the sample 1 can be evaluated. In the following, the evaluation method for the mouthfeel and the feeling of residue is described.

Figure 5:
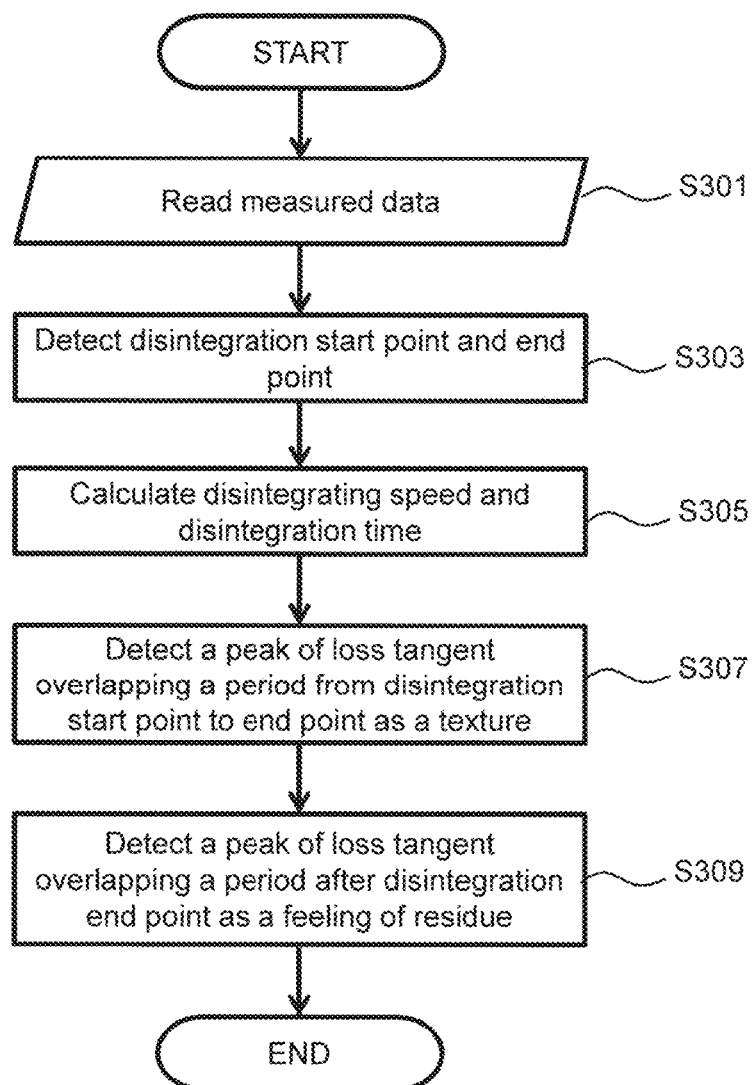
FIG. 5 is a flowchart showing an evaluation method for a mouthfeel and a feeling of residue of an orally disintegrating test object according to one embodiment of the present invention.

FIG. 5 is a flowchart showing the evaluation method for the mouthfeel and the feeling of residue of the orally disintegrating test object according to one embodiment of the present invention. The distance from the sample table 111 to the jig 113 and the loss tangent (tan δ) plotted on the time axis are read (S301).

The analyzing unit 130 detects the region A in which the distance from the sample table 111 increases on the curve where the distance (gap) from the jig 113 is plotted on the time axis. After the region A, the analyzing unit 130 detects a point where the distance (gap) from the sample table 111 to the jig 113 is changed to linearly decrease with respect to the time axis as a disintegration start point (time S). Also, on the curve where the distance (gap) from the jig 113 is plotted on the time axis, the analyzing unit 130 detects a point where the distance (gap) from the sample table 111 to the jig 113 is changed to mildly decrease with respect to the time axis as a disintegration end point (time E) (S303).

On the curve where the distance (gap) from the jig 113 is plotted on the time axis, the analyzing unit 130 calculates a disintegrating speed from a linear gradient between the disintegration start point (time S) and the disintegration end point (time E). Also, the analyzing unit 130 calculates a period from the disintegration start point (time S) to the disintegration end point (time E) as a disintegration time (S305).

The analyzing unit 130 determines the value (region B) of the loss tangent (tan δ) appearing in a period overlapping the period from the time S to the time E as a mouthfeel when the sample 1 orally disintegrates (S307). Also, the analyzing unit 130 detects the loss tangent (tan δ) in the region C as a feeling of residue (S309).

As has been described above, by using the evaluation method for a mouthfeel and a feeling of residue of the orally disintegrating test object according to the embodiment of the present invention, the mouthfeel and the feeling of residue at the time of oral disintegration of the sample 1 can be evaluated from the measured distance from the sample table 111 to the jig 113 and data of the loss tangent (tan δ) of the sample 1.

EXAMPLES

Specific examples and test results of the mouthfeel evaluation method for the orally disintegrating test object according to the present invention described above are described in more detail below.

An orally disintegrating tablet was prepared and arranged on a rheometer (manufactured by Anton Paar GmbH, MCR 302). 0.5 ml of water at 35° C. was dropped to the orally disintegrating tablet, and the distance (d) from the sample table 111 to the jig 113 and the loss tangent (tan δ) were measured. While the jig 113 is driven to give a distortion of 0.5% with a cycle of 3 Hz, any of three pressures, 1 N, 5 N, or 10 N, was applied to the orally disintegrating tablet, and the distance (d) from the sample table 111 to the jig 113 and the loss tangent (tan δ) were measured. The measured distance (d) and loss tangent (tan δ) were plotted on the time axis.

Figure 6:
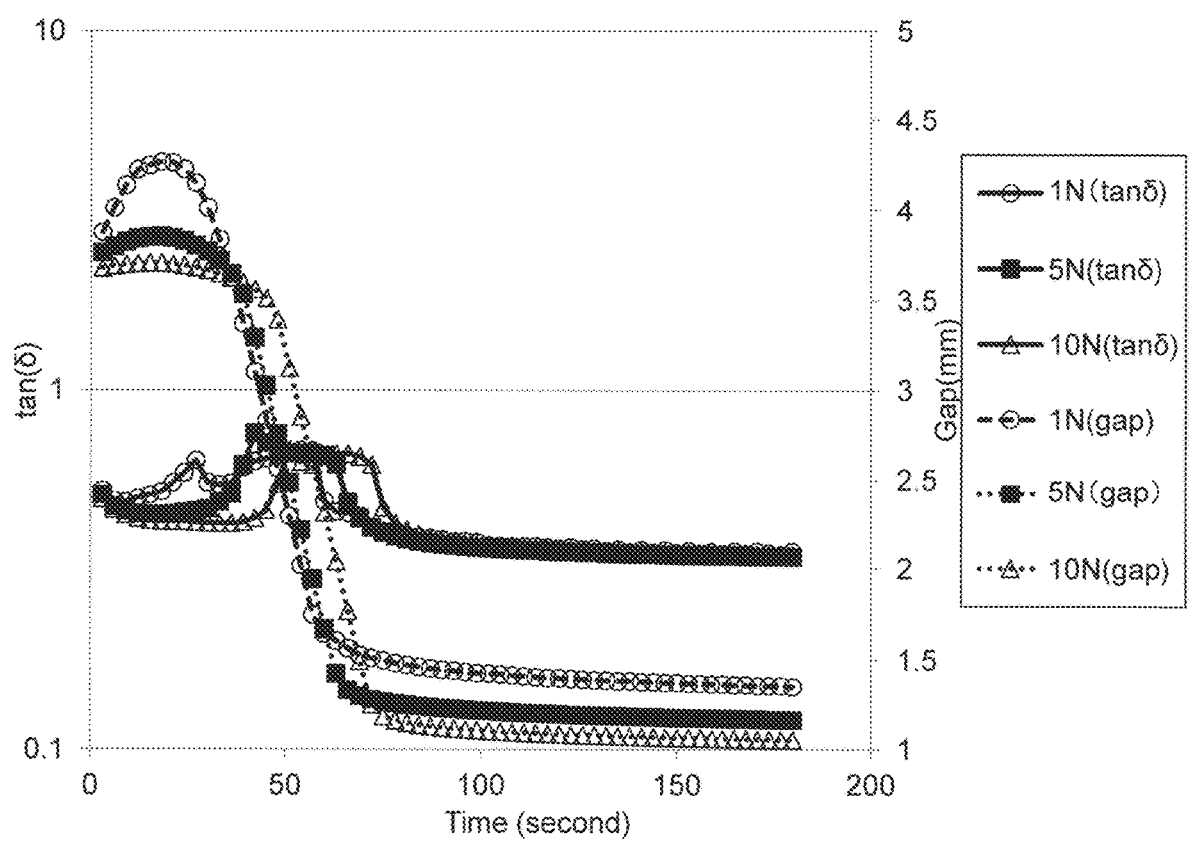
FIG. 6 is a diagram with a distance (d) from a sample table 111 to a jig 113 and a loss tangent (tan δ) measured with any of three pressures, 1 N, 5 N, or 10 N, applied thereto and plotted on a time axis, according to one embodiment of the present invention.

FIG. 6 is a diagram with the distance (d) (gap) from the sample table 111 to the jig 113 and the loss tangent (tan δ) measured with any of three pressures, 1 N, 5 N, or 10 N, applied thereto and plotted on the time axis. From the curve of the distance (d) (gap) from the sample table 111 to the jig 113 of FIG. 6, it can be found that the tongue pressure influences the disintegrating speed. On the other hand, from the result of the loss tangents (tan δ), it is demonstrated that, although the tongue pressure does not significantly influence the mouthfeel, a pressure of 5 N on the same degree of the human tongue pressure of 40 kPa is appropriate for measurement of the value of the region B for evaluating the mouthfeel (such as softness and smoothness) at the time of oral disintegration of the orally disintegrating tablet.

Next, orally disintegrating tablets (samples A to C) manufactured by mixing magnesium stearate into respective commercially-available premix additives of three types (A: GRANFILLER-D; B: PEARLITOL Flash; C: Pharmaburst 500) at 100:1 were prepared.

0.5 ml of water at 35° C. was dropped to each oral disintegrating tablet, and a pressure of 5 N was applied to the oral disintegrating tablet to measure the distance (d) from the sample table 111 to the jig 113, the loss tangent (tan δ), and the storage elastic modulus (G'). While the jig 113 was driven to give any of distortions, 0.1%, 0.2%, 0.5%, 5%, 10%, 20%, or 50% with a cycle 3 Hz, the distance (d) from the sample table 111 to the jig 113, the loss tangent (tan δ), and the storage elastic modulus (G') were measured. The distance (d), the loss tangent (tan δ), and the storage elastic modulus (G') were plotted on the time axis.

Figure 7A:
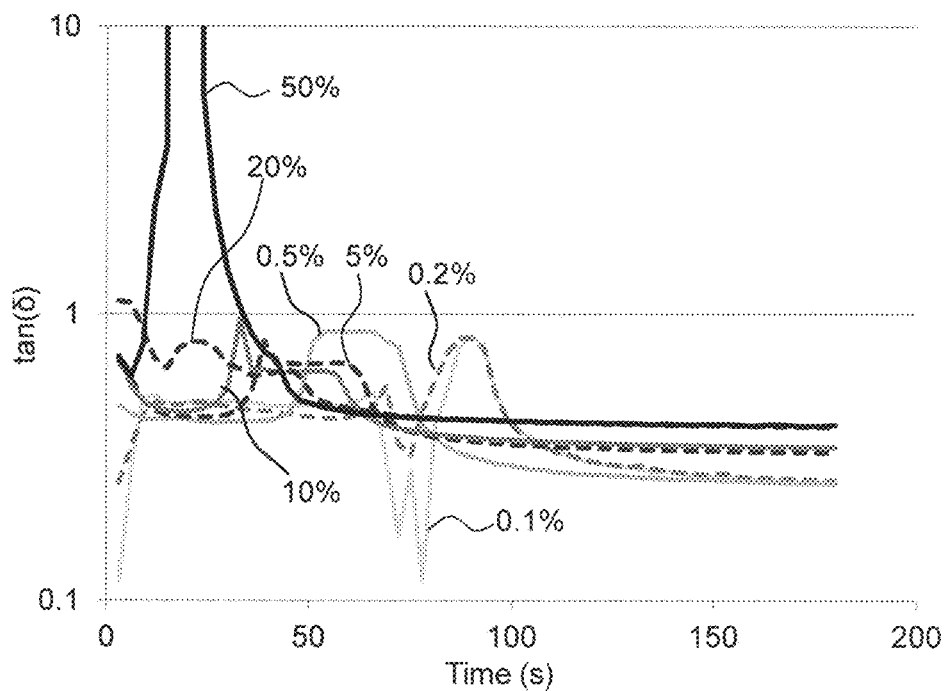
Figure 7B:
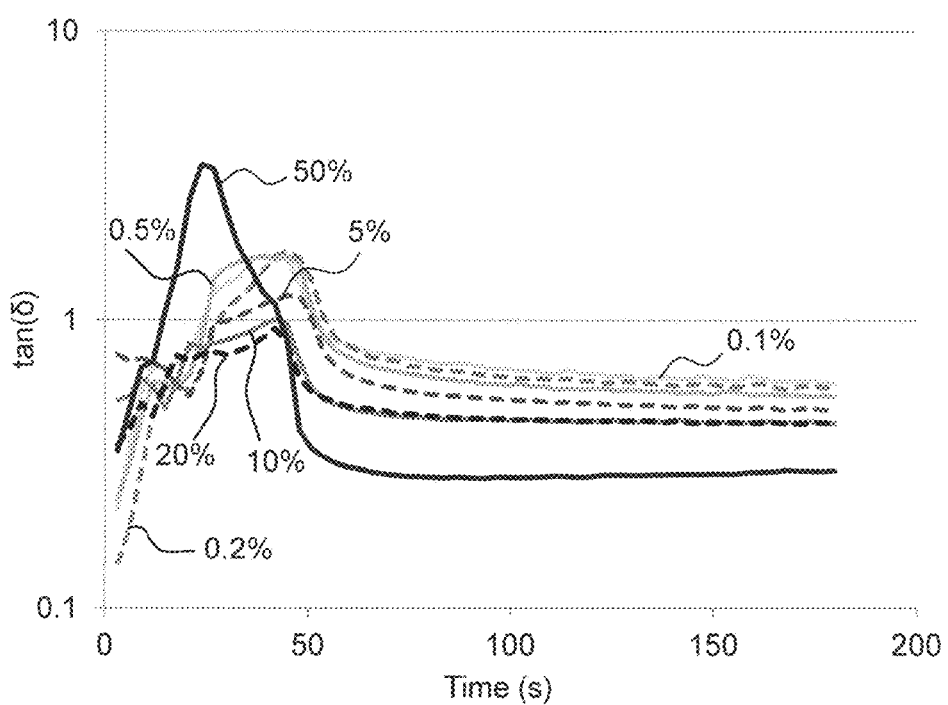
FIG. 7B shows measurement results using a sample B.
Figure 8:
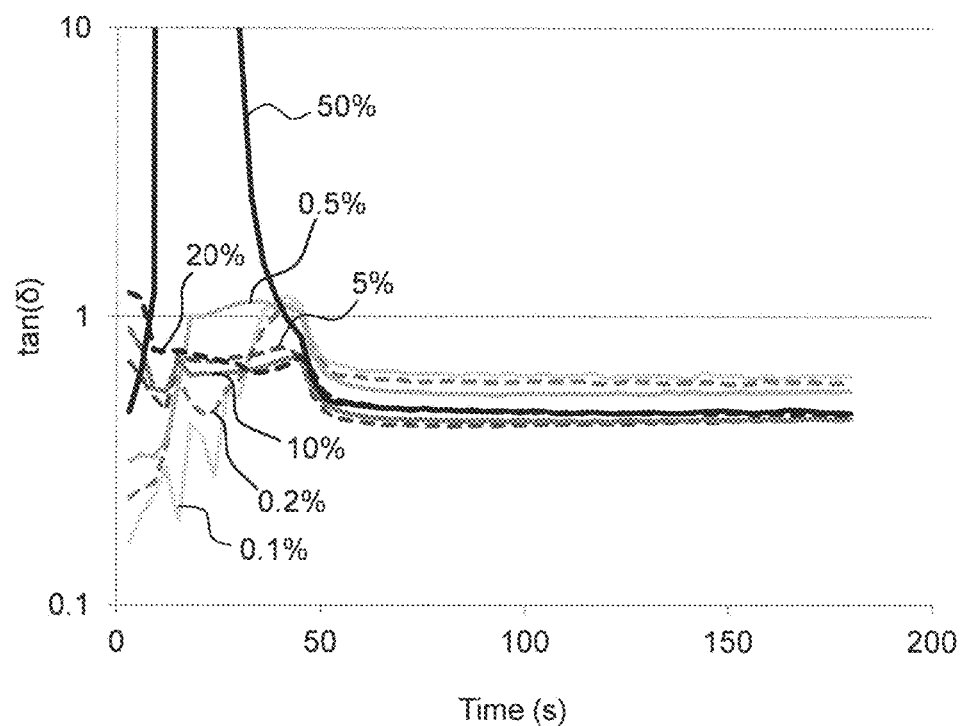
FIG. 8 is a diagram with distance (d) from the sample table 111 to the jig 113 to a sample C, a loss tangent (tan δ), and a storage elastic modulus (G') measured with any of distortions, 0.1%, 0.2%, 0.5%, 5%, 10%, 20%, or 50%, given to a sample C and plotted on the time axis according to one embodiment of the present invention.

FIG. 7A, FIG. 7B and FIG. 8 show diagrams with distance (d) from the sample table 111 to the jig 113, the loss tangent (tan δ), and the storage elastic modulus (G') measured with any of distortions, 0.1%, 0.2%, 0.5%, 5%, 10%, 20%, or 50%, given thereto and plotted on the time axis. FIG. 7A shows the measurement results using the sample A, and FIG. 7B shows the measurement results using the sample B. Also, FIG. 8 shows the measurement results using the sample C. From the curves of the loss tangent (tan δ) of FIG. 7A, FIG. 7B and FIG. 8, the jig 113 slipped with a distortion equal to or larger than 20% in the samples A and C to make accurate measurement impossible, but the jig 113 did not slip even with a distortion of 20% in the sample B to make measurement possible. Furthermore, it turned out that unknown behavior occurs with a distortion equal to or smaller than 0.2% in the sample A, but measurement was possible in the samples B and C even with a distortion of 0.1%. From these results, in the mouthfeel evaluation method for the orally disintegrating test object according to the present invention, it turned out that a distortion equal to or larger than 0.1% and equal to or smaller than 20% is preferable, although an appropriate range is varied depending on the characteristics of the sample.

Figure 9A:
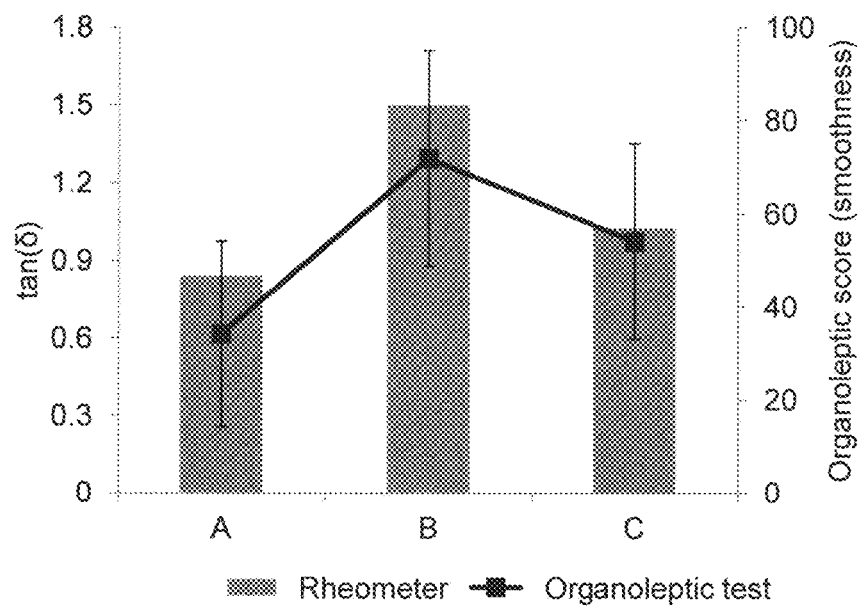
FIG. 9A shows diagrams in which values of a loss tangent (tan δ) of an orally disintegrating tablet and evaluation of smoothness by an organoleptic test are compared, according to one embodiment of the present invention.
Figure 9B:
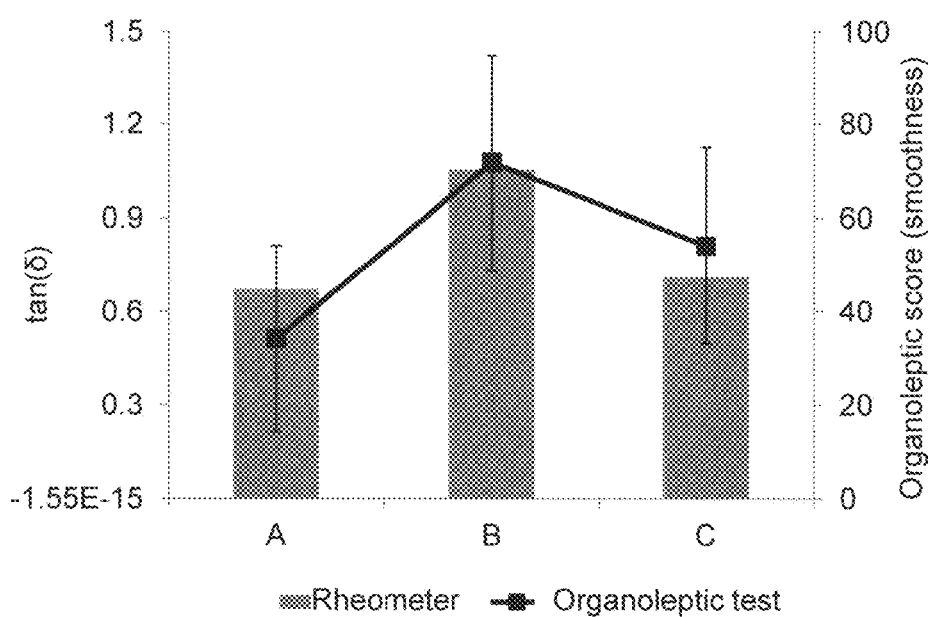
FIG. 9B shows diagrams in which values of a loss tangent (tan δ) of an orally disintegrating tablet and evaluation of smoothness by an organoleptic test are compared, according to one embodiment of the present invention.

Next, for the above-described samples A to C, the values of the loss tangent (tan δ) measured with distortions of 0.5% and 5% and smoothness by an organoleptic test were compared. FIG. 9A and FIG. 9B show diagrams in which the values of the loss tangent (tan δ) of the orally disintegrating tablet and evaluation of smoothness by the organoleptic test are compared. FIG. 9A shows the values of the loss tangent (tan δ) measured with a distortion of 0.5%, and FIG. 9B shows the values of the loss tangent (tan δ) measured with a distortion of 5%. From the results of FIG. 9A and FIG. 9B, it turned out that the values of the loss tangent (tan δ) measured with distortions of 0.5% and 5% have the most favorable correlation with evaluation of smoothness by the organoleptic test.

The amount of the test liquid to be added at the time of measurement has been studied. A sample A with an amount of water absorption of 0.230 ml and a sample B with an amount of water absorption of 0.100 ml were prepared. By using the samples A and B, the distance (d) from the sample table 111 to the jig 113, the loss tangent (tan δ), and the storage elastic modulus (G') were measured by changing the amount of water to be dropped. While water at 35° C. was dropped to the samples A and B and a distortion of 0.5% was given with a cycle of 3 Hz, a pressured of 5 N was applied to each sample to measure the distance (d) from the sample table 111 to the jig 113, the loss tangent (tan δ), and the storage elastic modulus (G').

Figure 10A:
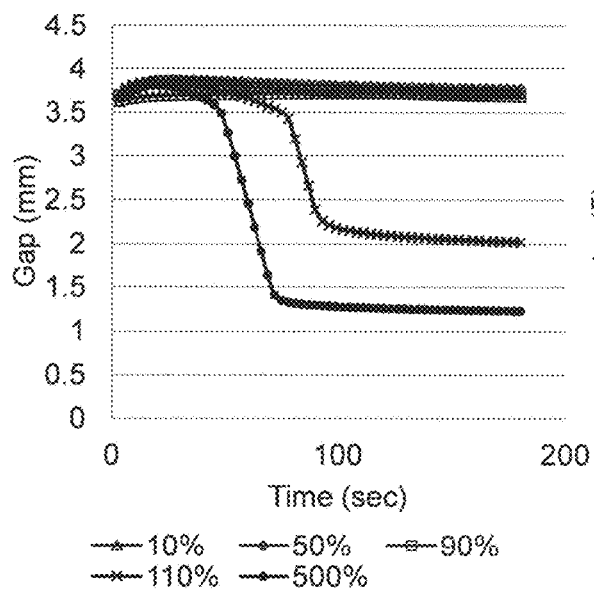
Figure 10B:
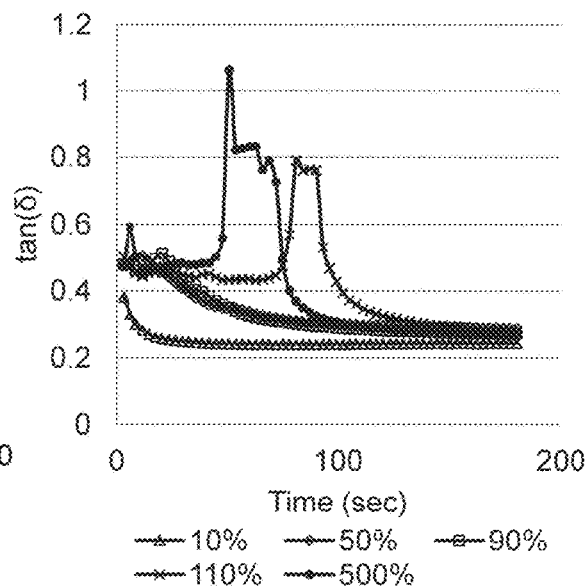
FIG. 10B shows measurement results of the loss tangent (tan δ).
Figure 10C:
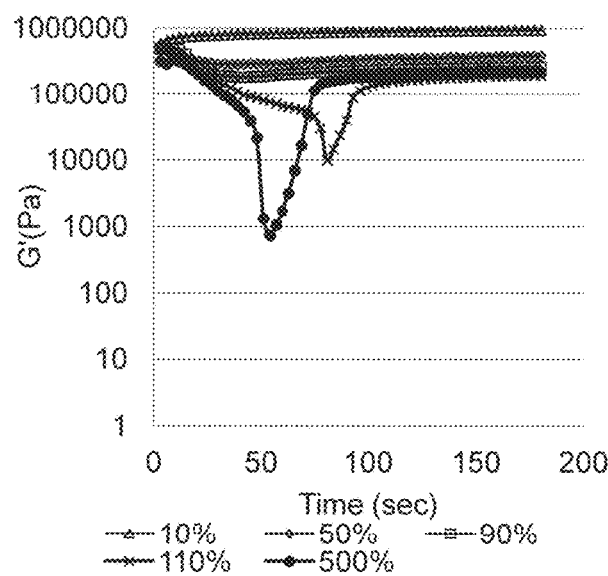
FIG. 10C shows measurement results of the storage elastic modulus (G').
Figure 11A:
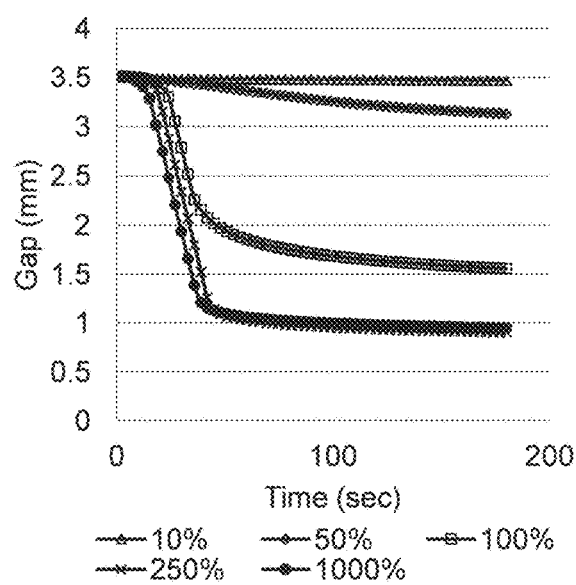
Figure 11B:
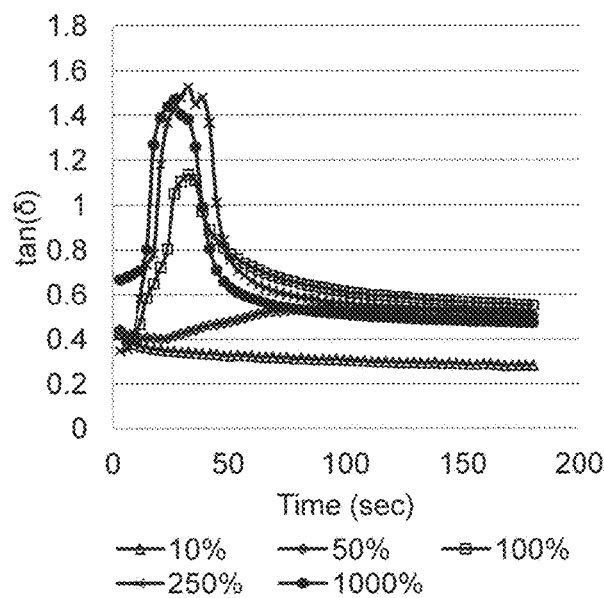
FIG. 11B shows measurement results of the loss tangent (tan δ).
Figure 11C:
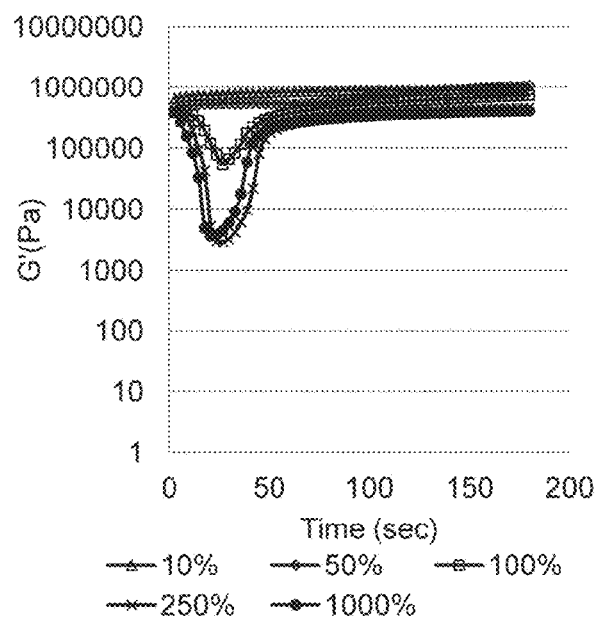
FIG. 11C shows measurement results of the storage elastic modulus (G').

The measurement results of the distance (d) from the sample table 111 to the jig 113, the loss tangent (tan δ), and the storage elastic modulus (G') for the sample A are shown in FIG. 10A to FIG. 10C. Also, the measurement results of the distance (d) from the sample table 111 to the jig 113, the loss tangent (tan δ), and the storage elastic modulus (G') for the sample B are shown in FIG. 11A to FIG. 11C. From the results of FIG. 10B and FIG. 11B, it turned out that changes are observed in the storage elastic modulus (G') and the loss tangent (tan δ) with 50% or more of the amount of absorbable water and the orally disintegrating tablet completely disintegrates with 100% or more.

Figure 12A:
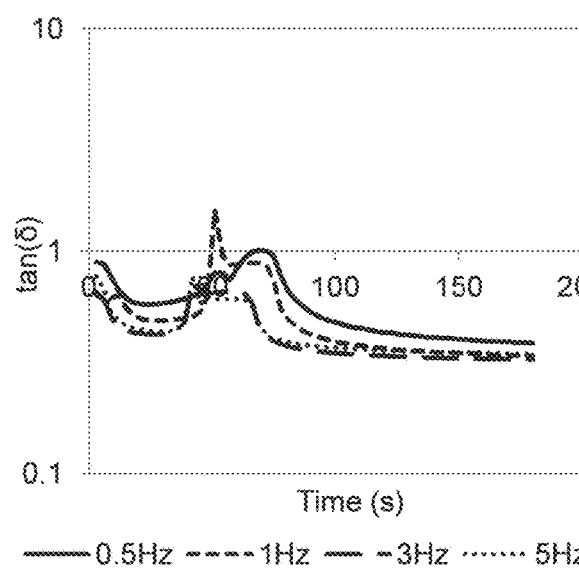
FIG. 12A is a diagram in which the loss tangent (tan δ) is measured with a cycle of giving a distortion being as 0.5 Hz, 1 Hz, 3 Hz, and 5 Hz, according to one embodiment of the present invention.
Figure 12B:
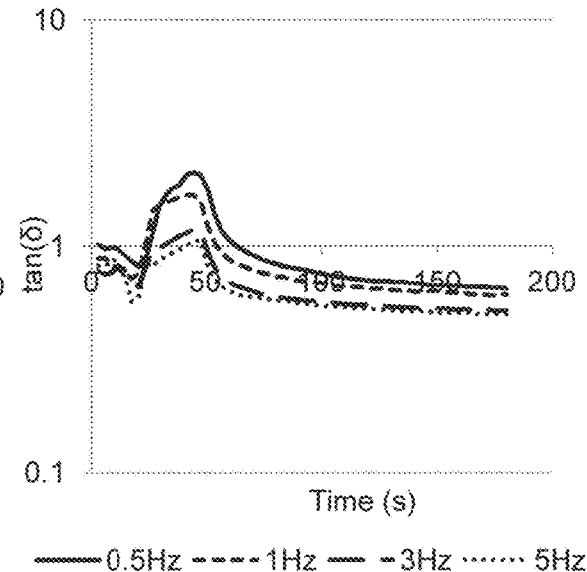
FIG. 12B is a diagram in which the loss tangent (tan δ) is measured with a cycle of giving a distortion being as 0.5 Hz, 1 Hz, 3 Hz, and 5 Hz, according to one embodiment of the present invention.
Figure 12C:
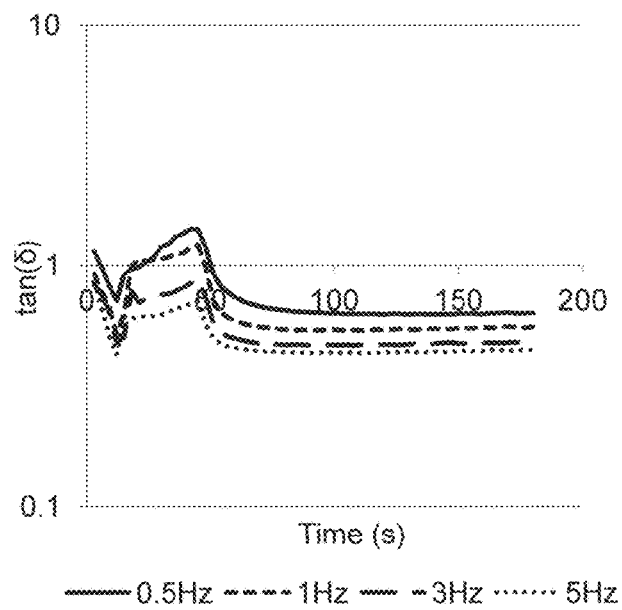
FIG. 12C is a diagram in which the loss tangent (tan δ) is measured with a cycle of giving a distortion being as 0.5 Hz, 1 Hz, 3 Hz, and 5 Hz, according to one embodiment of the present invention.

By using the above-described samples A to C, the loss tangent (tan δ) was measured with cycles of giving a distortion of 0.5 Hz, 1 Hz, 3 Hz, and 5 Hz. Note that the loss tangent (tan δ) was measured by dropping 0.5 mL of water at 35° C. to the samples A to C and giving a distortion of 5% in each cycle, and applying a pressure of 5 N. The measurement results for the samples A to C are shown in FIG. 12A to FIG. 12C, respectively. From the results of FIG. 12A to FIG. 12C, it turned out that mouthfeel evaluation is possible in a cycle range equal to or larger than 0.5 Hz and equal to or smaller than 5 Hz.

According to one embodiment of the present invention, an evaluation method is provided for evaluating a mouthfeel of drugs such as orally disintegrating tablets, powder, and granule and orally disintegrating foods such as tablet sweets in a simulated intraoral environment. Also, according to one embodiment of the present invention, an evaluation apparatus is provided for evaluating a mouthfeel of orally disintegrating drugs and foods such as orally disintegrating tablets and tablet sweets in a simulated intraoral environment.

What is claimed is:

1. A mouthfeel evaluation method for an orally disintegrating test object, the method comprising:
    giving a predetermined distortion with a predetermine cycle as applying a predetermined pressure to the orally disintegrating test object by a measurement apparatus;
    adding a predetermined amount of a test liquid to the test object by the measurement apparatus; and
    measuring a loss tangent of the test object with time by the measurement apparatus.

2. The mouthfeel evaluation method for the orally disintegrating test object according to claim 1, wherein
    when a jig of ϕ12 mm is used, the pressure to be applied to the test object is larger than 1 N and smaller than 10 N.

3. The mouthfeel evaluation method for the orally disintegrating test object according to claim 2, wherein
    the distortion equal to or larger than 0.1% and equal to or smaller than 20% is given to the test object with a cycle equal to or larger than 0.5 Hz and equal to or smaller than 5 Hz.

4. The mouthfeel evaluation method for the orally disintegrating test object according to claim 3, wherein
    the test liquid equal to or larger than 50% of an amount absorbable by the test object is added.

5. The mouthfeel evaluation method for the orally disintegrating test object according to claim 2, wherein
    the test liquid equal to or larger than 50% of an amount absorbable by the test object is added.

6. The mouthfeel evaluation method for the orally disintegrating test object according to claim 1, wherein
    the test liquid equal to or larger than 50% of an amount absorbable by the test object is added.

7. The mouthfeel evaluation method for the orally disintegrating test object according to any one of claim 1, wherein
    a mouthfeel is evaluated with a value of the loss tangent until the test object disintegrates, and
    a feeling of residue is evaluated with a value after the test object disintegrates.

8. A mouthfeel evaluation apparatus for an orally disintegrating test object, the apparatus comprising:
    a viscoelasticity measurement unit giving a predetermined distortion with a predetermine cycle as applying a predetermined pressure to the orally disintegrating test object and measures a loss tangent of the test object with time;
    a test liquid supply unit adding a predetermined amount of a test liquid to the test object; and
    an analyzing unit analyzing characteristics of the test object.

9. The mouthfeel evaluation apparatus for the orally disintegrating test object according to claim 8, wherein
    the viscoelasticity measurement unit includes a jig of ϕ12 mm, and applies to the test object a pressure larger than 1 N and smaller than 10 N.

10. The mouthfeel evaluation apparatus for the orally disintegrating test object according to claim 9, wherein
    the viscoelasticity measurement unit gives to the test object a distortion equal to or larger than 0.1% and equal to or smaller than 20% with a cycle equal to or larger than 0.5 Hz and equal to or smaller than 5 Hz.

11. The mouthfeel evaluation apparatus for the orally disintegrating test object according to claim 10, wherein
    the test liquid supply unit adds to the test object the test liquid equal to or larger than 50% of an amount absorbable by the test object.

12. The mouthfeel evaluation apparatus for the orally disintegrating test object according to claim 9, wherein
the test liquid supply unit adds to the test object the test liquid equal to or larger than 50% of an amount absorbable by the test object.

13. The mouthfeel evaluation apparatus for the orally disintegrating test object according to claim 8, wherein
the test liquid supply unit adds to the test object the test liquid equal to or larger than 50% of an amount absorbable by the test object.

14. The mouthfeel evaluation apparatus for the orally disintegrating test object according to any one of claim 8, wherein
the analyzing unit presents a mouthfeel as a value of the loss tangent until the test object disintegrates, and
the analyzing unit presents a feeling of residue as a value after the test object disintegrates.

* * * * *